US009521483B2

(12) United States Patent
Hallberg et al.

(10) Patent No.: US 9,521,483 B2
(45) Date of Patent: Dec. 13, 2016

(54) WEARABLE PHYSIOLOGICAL ACOUSTIC SENSOR

(71) Applicant: Sharp Laboratories of America, Inc., Camas, WA (US)

(72) Inventors: Bryan Severt Hallberg, Vancouver, WA (US); Glenn Peter Piekstra, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 376 days.

(21) Appl. No.: 14/159,663

(22) Filed: Jan. 21, 2014

(65) Prior Publication Data

US 2015/0208163 A1 Jul. 23, 2015

(51) Int. Cl.
*A61B 7/04* (2006.01)
*H04R 1/46* (2006.01)

(52) U.S. Cl.
CPC ............. *H04R 1/46* (2013.01); *H04R 2410/05* (2013.01)

(58) Field of Classification Search
CPC ....... H04R 1/46; A61B 5/6802; A61B 5/6832; A61B 5/6833
USPC ............................................. 381/67; 181/131
See application file for complete search history.

(56) References Cited

U.S. PATENT DOCUMENTS

| | | | | |
|---|---|---|---|---|
| 5,539,831 | A * | 7/1996 | Harley | 381/67 |
| 5,774,563 | A * | 6/1998 | DesLauriers | A61B 7/04 381/67 |
| 2005/0094832 | A1* | 5/2005 | Song et al. | 381/174 |
| 2005/0245839 | A1* | 11/2005 | Stivoric et al. | 600/549 |
| 2007/0165885 | A1 | 7/2007 | Chou | |
| 2008/0232605 | A1* | 9/2008 | Bagha | 381/67 |
| 2010/0274099 | A1 | 10/2010 | Telfort et al. | |
| 2010/0276215 | A1* | 11/2010 | Duheille et al. | 178/18.04 |
| 2011/0034831 | A1 | 2/2011 | Christensen et al. | |
| 2011/0060196 | A1* | 3/2011 | Stafford | A61B 5/0002 600/309 |
| 2011/0125060 | A1 | 5/2011 | Telfort et al. | |
| 2011/0213272 | A1 | 9/2011 | Telfort et al. | |
| 2011/0213274 | A1 | 9/2011 | Telfort et al. | |

* cited by examiner

*Primary Examiner* — Paul S Kim
*Assistant Examiner* — Katherine Faley
(74) *Attorney, Agent, or Firm* — Scot A. Reader

(57) ABSTRACT

A wearable physiological acoustic sensor has an embedded and stacked acoustic sensing component architecture that inhibits motion-related impulse noise and environmental background noise, and provides good body sound capture, good patient comfort and an unobtrusive presence. The embedded and stacked component architecture also includes an environmental microphone that enables cancellation of background noise for further noise reduction.

17 Claims, 3 Drawing Sheets

WEARABLE PHYSIOLOGICAL ACOUSTIC SENSOR

BACKGROUND OF THE INVENTION

The present invention relates to acoustic sensors and, more particularly, wearable physiological acoustic sensors.

Physiological acoustic sensors gather physiological sounds from the human body that can be applied to a variety of health diagnostic purposes. For example, heart and lung sounds can be used to estimate vital sign values, such as heart rate and respiration rate. Heart and lung sounds can also be used to detect a host of health problems. For example, heart sounds can be used to identify heart anomalies, such as presence of the S3, S4 sounds, splits of the Si and S2 sounds, rubs, click and heart murmurs that indicate mitral or aortic regurgitation, mitral or aortic stenosis or patent ductos arteriosus. Lung sounds can be used to identify breathing anomalies, such as wheeze, stridor, grasp, rales and crackles. Additionally, physiological acoustic sensors can detect other organ sounds of interest, such as sounds indicating the start of digestive cycles that can be used to set optimal feeding schedules for comatose patients.

Some physiological acoustic sensors, such as electronic stethoscopes, gather physiological sounds in episodic spot checks. These sensors are not wearable by the person being monitored and do not provide continuous, real-time monitoring of vital sign values or health diagnostics.

Other physiological acoustic sensors are mounted on the body or worn on clothing of the person being monitored. While conventional wearable sensors can provide continuous, real-time monitoring, they are often highly susceptible to impulse noise from abrupt hits, clothing scrapes and other motion-related events as well as background noise from the surrounding environment. Moreover, these conventional sensors often have a large form factor which does not keep close enough proximity between the body microphone and the body of patients to provide good body sound capture, subjects patients to discomfort and provides an intrusive presence.

SUMMARY OF THE INVENTION

The present invention provides a wearable physiological acoustic sensor having an embedded and stacked acoustic sensing component architecture that inhibits motion-related impulse noise and environmental background noise, and provides good body sound capture, good patient comfort and an unobtrusive presence. The embedded and stacked component architecture also includes an environmental microphone that enables cancellation of background noise for further noise reduction.

In one aspect of the invention, a wearable physiological acoustic sensor comprises a plaster and an acoustic sensing component assembly. The plaster has a top layer and a bottom layer. The component assembly has an acoustic sensing component housing and an acoustic sensing component stack embedded in the component housing. The component housing has a ceiling, a wall and a floor having a flange held between the top layer and the bottom layer. The component stack has a body microphone with acoustic access through an opening in the floor and an environmental microphone with acoustic access through an opening in the ceiling.

In some embodiments, the component stack has a body microphone printed circuit board.

In some embodiments, the component assembly has a lower orifice running from the body microphone through the body microphone printed circuit board providing the body microphone with acoustic access.

In some embodiments, the lower orifice runs from the body microphone to a body sound chamber disposed between the lower orifice and the floor.

In some embodiments, the component stack has an environmental microphone printed circuit board.

In some embodiments, the component assembly has an upper orifice running from the environmental microphone through the environmental microphone printed circuit board providing the environmental microphone with acoustic access.

In some embodiments, the upper orifice runs from the environmental microphone to the ceiling.

In some embodiments, the body microphone and the environmental microphone are acoustically isolated from one another.

In some embodiments, acoustic isolation tape is disposed between the body microphone and the environmental microphone.

In some embodiments, the component housing has a strain relief element projecting from the wall and the component assembly has an acoustic signal output line running through an opening in the strain relief element.

In some embodiments, the flange is snugly retained between the top layer and the bottom layer.

In some embodiments, the plaster has a preformed groove and the flange is held in the preformed groove.

In some embodiments, the bottom layer comprises adhesive transfer tape having adhesive on a top side and a bottom side, wherein the top side adheres to the top layer.

In some embodiments, the plaster has a removable protective backing that adheres to the bottom layer.

In some embodiments, the component housing is centered on the plaster.

In some embodiments, the component housing is made of silicone.

In some embodiments, the component housing is substantially cylindrical.

In another aspect of the invention, an acoustic sensing component assembly for a physiological acoustic sensor comprises an acoustic sensing component housing having a ceiling, a wall and a floor having a mounting flange; and an acoustic sensing component stack embedded in the component housing including a body microphone with acoustic access through an opening in the floor and an environmental microphone with acoustic access through an opening in the ceiling.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
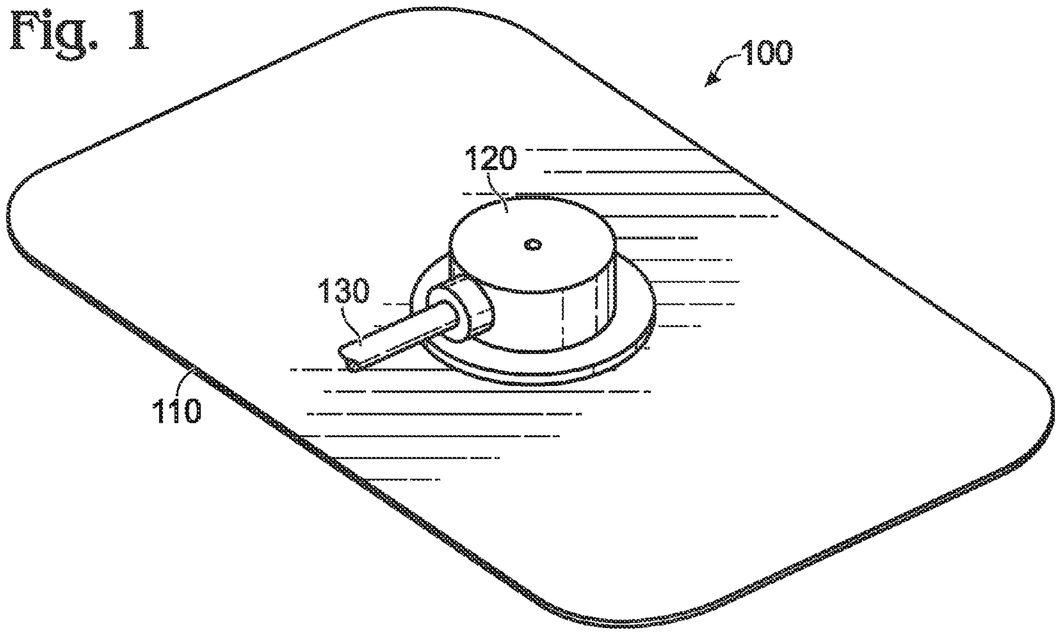
FIG. 1 is a top perspective view of a wearable physiological acoustic sensor.

FIG. 1 shows a wearable physiological acoustic sensor 100 in some embodiments of the invention. Sensor 100 has a plaster 110 for adhering to the body of a person being monitored (i.e. patient) at a detection point, such as the chest, back or neck. Plaster 110 has a top layer and a bottom layer. The bottom layer adheres to the patient when sensor 100 is in use. Sensor 100 also has an acoustic sensing component housing 120 centrally located on plaster 110. Component housing 120 embeds an acoustic sensing component stack that gathers physiological sounds. The component stack has a body microphone that collects physiological sounds, such as heart and lung sounds, emanating from the body of a patient and uses them for various purposes, such as determining vital sign values and diagnosing health maladies from anomalous physiological sounds. In addition to the body microphone, the component stack also has an environmental microphone that collects environmental sounds to enable noise cancellation. The body microphone has acoustic access to physiological sounds through an opening in the floor of component housing 120 (and plaster 110). The environmental microphone has acoustic access to environmental sounds through an opening in the ceiling of component housing 120. An acoustic signal output line 130 carrying detected physiological and environmental sounds runs through an opening in the wall of component housing 120 and terminates at a remote acoustic signal acquisition or processing device.

Figure 2:
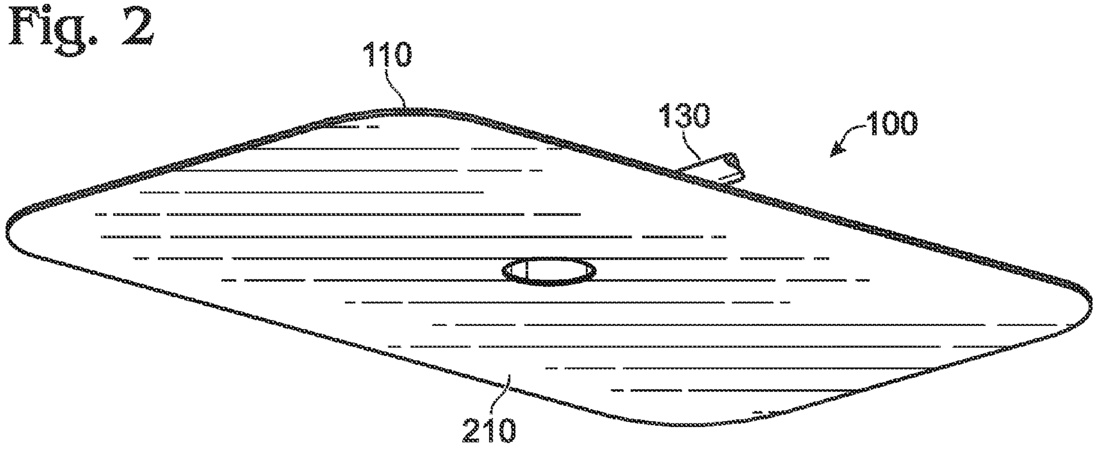
FIG. 2 is a bottom perspective view of the sensor.

FIG. 2 is a bottom view of sensor 100. The bottom layer 210 of plaster 110 has a top side that adheres to the top layer of plaster 110 and a bottom side that adheres to the patient. In some embodiments, bottom layer 210 is medical grade tape having adhesive on both sides. In some embodiments, plaster 110 has a removable protective backing that adheres to the bottom side of bottom layer 210 and protects the adhesive on the bottom side of bottom layer 210 when sensor 100 is not in use. Bottom layer 210 has a centrally located opening providing acoustic access to the body microphone embedded in component housing 120.

Figure 3:
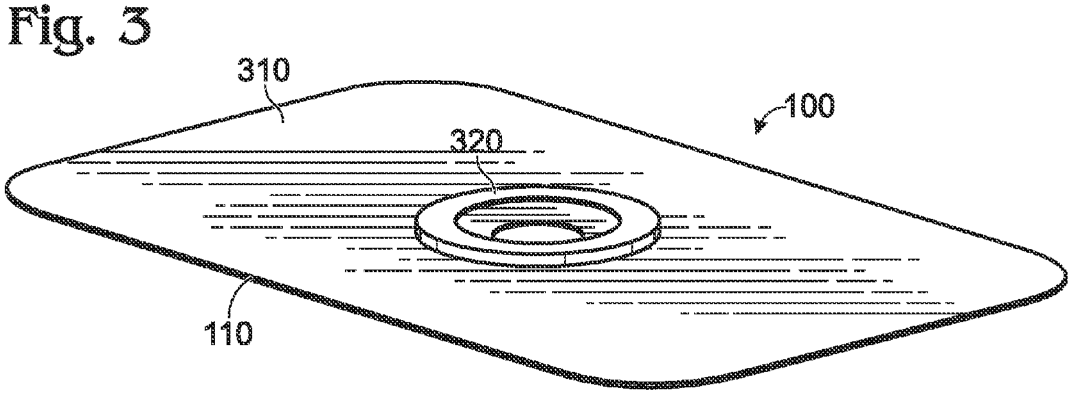
FIG. 3 is a top perspective view of the plaster of the sensor.
Figure 4:
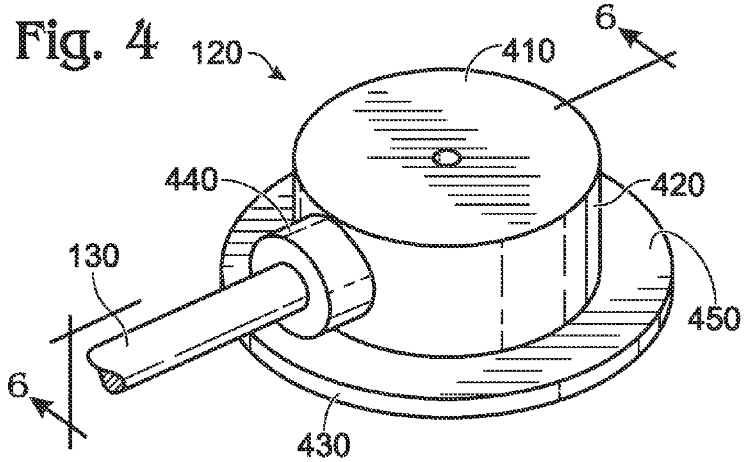
FIG. 4 is a top perspective view of the acoustic sensing component housing of the sensor.

FIG. 3 shows plaster 110 apart from component housing 120. Plaster 110 has a preformed groove 320 formed from top layer 310 and bottom layer 210. Referring to FIGS. 3 and 4 together, a flange 450 on component housing 120 is held within groove 320 whereby component housing 120 is mounted to plaster 110. In some embodiments, groove 320 is preformed at a raised surface of top layer 310 surrounding a centrally located opening in top layer 310 and is sized to accommodate flange 450. In other embodiments, flange 450 is centrally mounted to plaster 110 without constructing a preformed groove on plaster 110. In these embodiments, material elasticity of plaster 110 allows plaster 110 to deform and accommodate flange 450 between top layer 310 and bottom layer 210 at a central opening on top layer 310. In either event, flange 450 is snugly retained at the center of plaster 110 between top layer 310 and bottom layer 210.

FIG. 4 shows component housing 120 in more detail. Component housing 120 is a substantially cylindrical enclosure made of medical grade silicone having a ceiling 410, a wall 420 and a floor 430. Floor 430 includes the aforementioned flange 450 that is snugly retained between top layer 310 and bottom layer 210 of plaster 110 whereby component housing 120 is mounted to plaster 110. Ceiling 410 has an opening providing an environmental microphone embedded in component housing 120 with acoustic access to the surrounding environment through an upper orifice in component assembly. Component housing 120 also has a strain relief element 440 projecting from wall 420 which helps prevent acoustic signal output line 130 from separating from component housing 120.

Figure 5:
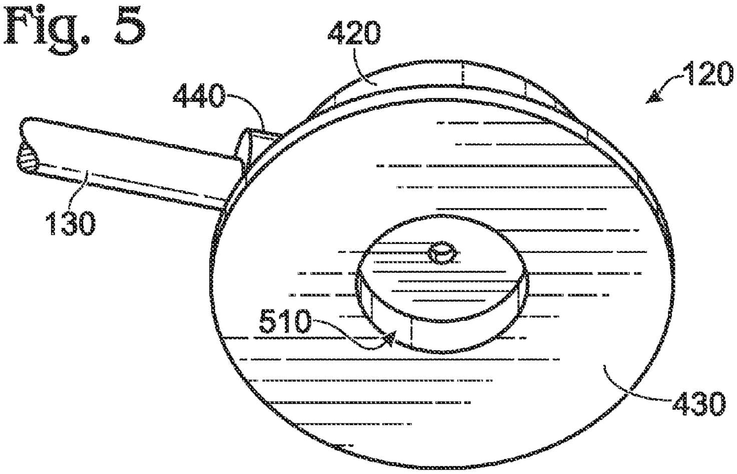
FIG. 5 is a bottom perspective view of the component housing.

FIG. 5 is a bottom view of component housing 120. Component housing 120 has a centrally located body sound chamber 510 surrounded by floor 430. When component housing 120 is mounted to plaster 110 and plaster 110 is adhered to the body of a patient, body sound chamber 510 hovers directly above the opening in bottom layer 210. The ceiling of body sound chamber 510 has an opening providing a body microphone embedded in component housing 120 with acoustic access to body sound chamber 510 through a lower orifice.

Figure 6:
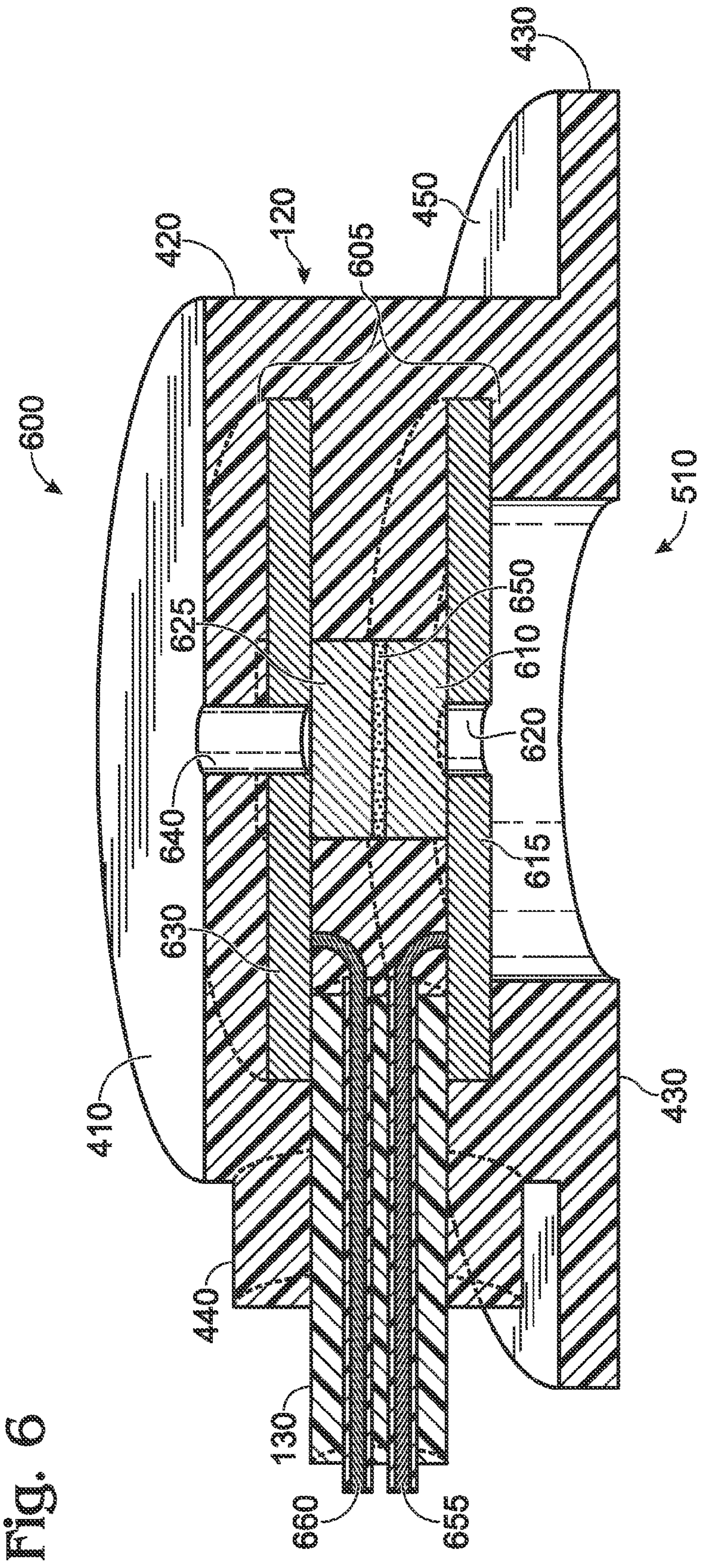
FIG. 6 is a cross sectional view of an acoustic sensing component assembly including the component housing and an embedded acoustic sensing component stack.

FIG. 6 provides a cross-sectional view of an acoustic sensing component assembly 600. Component assembly 600 includes component housing 120 and an acoustic sensing component stack 605 embedded in component housing 120. Component housing 120 is made of medical grade silicone. The bottom section of component stack 605 includes a body microphone 610 connected to a body microphone printed circuit board 615. When component housing 120 is mounted to plaster 110 and plaster 110 is adhered to the body of a patient, physiological sounds from the patient collect in body sound chamber 510. Body microphone 610 has acoustic access to and captures these physiological sounds through a lower orifice 620 running from body microphone 610 through body microphone printed circuit board 615 to body sound chamber 510. The top section of component stack 605 includes an environmental microphone 625 connected to an environmental microphone printed circuit board 630. Environmental microphone 625 has acoustic access to and captures environmental sounds through an upper orifice 640 running from environmental microphone 625 through environmental microphone printed circuit board 630 and component housing 120 to an opening in ceiling 410. Acoustic isolation tape 650 between microphones 610, 625 inhibits noise transfer between microphones 610, 625.

Component assembly 600 further includes acoustic signal wires 655, 660 carrying digitized acoustic signals embodying sounds captured by microphones 610, 625. Acoustic signal wires 655, 660 run from circuit boards 615, 630 into acoustic signal output line 130. Alternatively, digitized signals embodying sounds captured by microphones 610, 625 may be carried on the same set of wires using an audio data protocol such as $I^2S$. Circuit boards 615, 630 may be electrically connected to each other via wires, an inter-PCB connector, flex PCB material, or by other means. Acoustic signal output line 130 leaves component assembly 600 through an opening in strain relief element 440 and terminates at a remote acoustic signal acquisition or processing device. Alternatively, output line 130 may terminate at an intermediate device which connects to another cable or series of cables that eventually terminate at a remote acoustic signal acquisition or processing device, or which connects wirelessly to a remote acoustic signal acquisition or processing device.

In an exemplary embodiment, components of sensor 100 have the following dimensions:

Component housing diameter at floor=19 mm;

Component housing diameter at wall=13 mm;

Body mic and environmental mic printed circuit board diameter=10 mm;

Flange height=1 mm;

Component housing height=6.5 mm;

Body sound chamber diameter=7 mm;

Body sound chamber height=2 mm.

It will be appreciated by those of ordinary skill in the art that the invention can be embodied in other specific forms without departing from the spirit or essential character hereof. By way of example, the component housing may have other than a substantially cylindrical geometry, such as a substantially cubical one. As another example, the acoustic sensing components may be stacked in a different order. The present description is considered in all respects to be illustrative and not restrictive. The scope of the invention is indicated by the appended claims, and all changes that come within the meaning and range of equivalents thereof are intended to be embraced therein.

What is claimed is:

1. A wearable physiological acoustic sensor, comprising:

a plaster having a top layer and a bottom layer; and an acoustic sensing component assembly including a component housing having a ceiling, a wall and a floor having a flange held between the top layer and the bottom layer, and further including a component stack embedded in the component housing having a body microphone configured to collect airborne body sounds received through an opening in the floor and in the bottom layer and an environmental microphone configured to collect environmental sounds received through an opening in the ceiling.

2. The sensor of claim 1, wherein the component stack has a body microphone printed circuit board.

3. The sensor of claim 2, wherein the component assembly has a lower orifice running from the body microphone through the body microphone printed circuit board providing the body microphone with access to the airborne body sounds.

4. The sensor of claim 3, wherein the lower orifice runs from the body microphone to a body sound chamber disposed between the lower orifice and the floor.

5. The sensor of claim 1, wherein the component stack has an environmental microphone printed circuit board.

6. The sensor of claim 5, wherein the component assembly has an upper orifice running from the environmental microphone through the environmental microphone printed circuit board providing the environmental microphone with acoustic access.

7. The sensor of claim 6, wherein the upper orifice runs from the environmental microphone to the ceiling.

8. The sensor of claim 1, wherein the body microphone and the environmental microphone are acoustically isolated from one another.

9. The sensor of claim 1, wherein acoustic isolation tape is disposed between the body microphone and the environmental microphone.

10. The sensor of claim 1, wherein the component housing has a strain relief element projecting from the wall and the component assembly has an acoustic signal output line running through an opening in the strain relief element.

11. The sensor of claim 1, wherein the flange is snugly retained between the top layer and the bottom layer.

12. The sensor of claim 1, wherein the plaster has a preformed groove and the flange is held in the preformed groove.

13. The sensor of claim 1, wherein the plaster has a removable protective backing that adheres to the bottom layer.

14. The sensor of claim 1, wherein the component housing is centered on the plaster.

15. The sensor of claim 1, wherein the component housing is made of silicone.

16. The sensor of claim 1, wherein the component housing is substantially cylindrical.

17. A wearable physiological acoustic sensor, comprising:

an acoustic sensing component housing having a ceiling, a wall and a floor forming an enclosure and a mounting flange circumnavigating the housing;

a plaster having a groove holding the mounting flange; and an acoustic sensing component stack within the enclosure having a body microphone configured to collect airborne body sounds through aligned openings in the floor of the housing and the plaster and an environmental microphone configured to collect environmental sounds received through an opening in the ceiling of the housing.

* * * * *